United States Patent [19]

Discko, Jr.

[11] Patent Number: 5,052,927

[45] Date of Patent: Oct. 1, 1991

[54] SYRINGE AND DISPOSABLE CAPSULE WITH CANNULA FOR USE THEREWITH

[76] Inventor: John Discko, Jr., 50 Laura Rd., Hamden, Conn. 06514

[21] Appl. No.: 261,600

[22] Filed: Oct. 24, 1988

[51] Int. Cl.$^5$ .............................................. A61C 5/04
[52] U.S. Cl. ....................................... 433/90; 604/243
[58] Field of Search ................... 433/89, 90; 604/239, 604/240, 241, 243

[56] References Cited

U.S. PATENT DOCUMENTS

| | | | |
|---|---|---|---|
| 1,139,975 | 5/1915 | Hopper | 604/241 |
| 1,604,224 | 10/1926 | Friedman | 604/241 X |
| 1,734,154 | 11/1929 | Brown | 604/241 X |
| 2,034,294 | 3/1936 | Hein | 604/243 X |
| 2,505,028 | 4/1950 | Boeger | 604/239 X |
| 3,150,661 | 9/1964 | Maki | 604/243 X |
| 3,290,946 | 12/1966 | Pursell | 604/241 X |
| 3,364,002 | 1/1968 | Michel | 604/240 X |
| 3,382,865 | 5/1968 | Worrall, Jr. | 604/241 X |
| 3,581,399 | 6/1971 | Dragan | 433/90 |
| 3,611,573 | 10/1971 | Crawford et al. | 433/90 X |
| 3,921,864 | 11/1975 | Dawes | 604/241 X |
| 4,002,174 | 1/1977 | Reed et al. | 604/239 |
| 4,391,590 | 7/1983 | Dougherty | 433/90 |
| 4,404,862 | 9/1983 | Harris, Sr. | 604/241 X |
| 4,457,712 | 7/1984 | Dragan | 433/90 |
| 4,472,141 | 9/1984 | Dragan | 433/90 |
| 4,540,405 | 9/1985 | Miller et al. | 604/241 X |
| 4,768,954 | 9/1988 | Dragan | 433/90 |
| 4,874,378 | 10/1989 | Hillstead | 604/167 |

FOREIGN PATENT DOCUMENTS 818831 10/1951 Fed. Rep. of Germany ...... 604/240

Primary Examiner—Robert P. Swiatek
Assistant Examiner—Nicholas D. Lucchesi
Attorney, Agent, or Firm—Arthur T. Fattibene; Paul A. Fattibene

[57] ABSTRACT

A dental syringe and disposable capsule for dispensing a dental material wherein the capsule includes a reservoir portion containing a predetermined amount of material to be dispensed, and which reservoir is connected in communication with a discharge tip. Connected to the end of the tip and projecting therethrough is a needle cannula through which the material is ejected. A displaceable piston, which seals the material within the reservoir portion, is provided to force the material through the cannula when displaced within the reservoir portion. The arrangement is such that the cannula connection within the tip end permits the cannula to be rotatably mounted relative to the tip while maintaining a seal between the tip and the cannula.

18 Claims, 1 Drawing Sheet

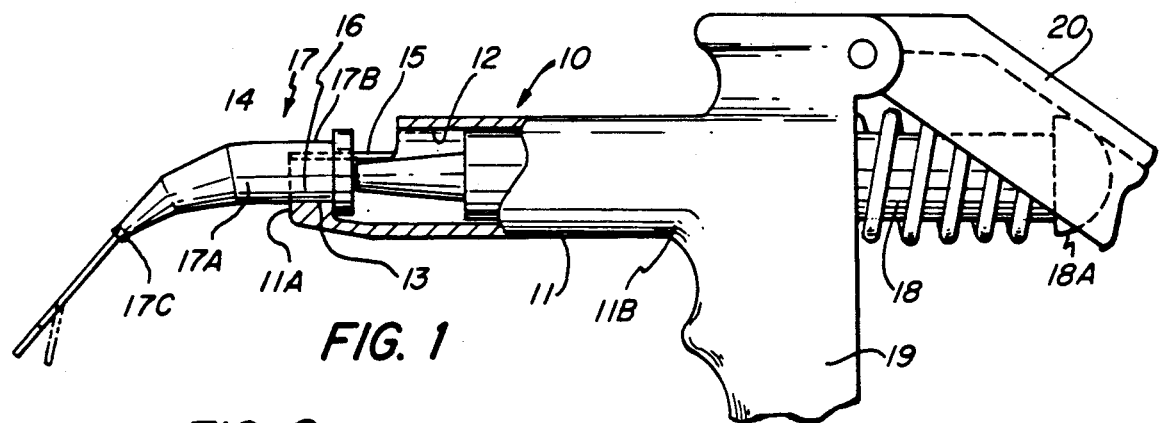
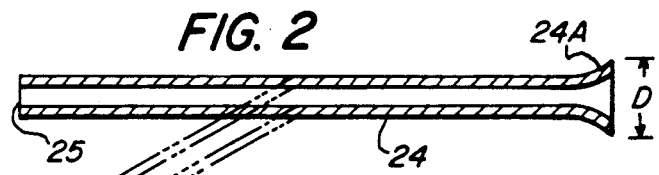
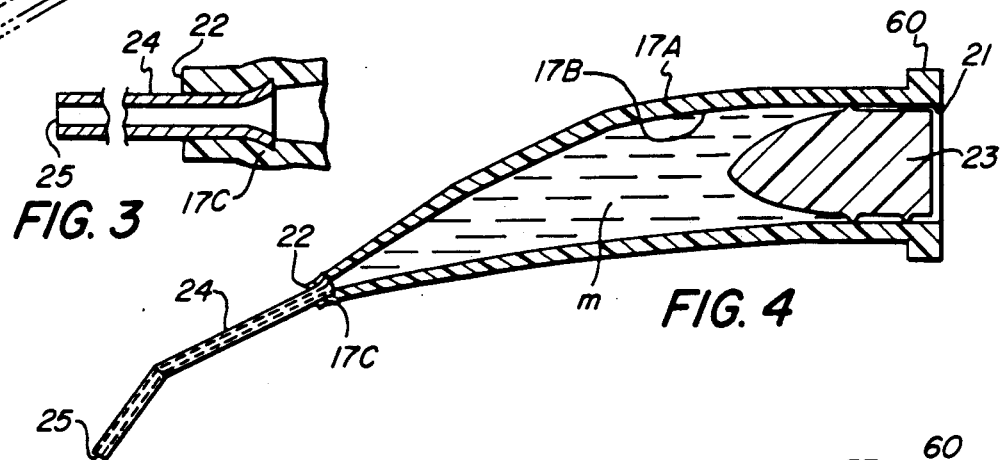
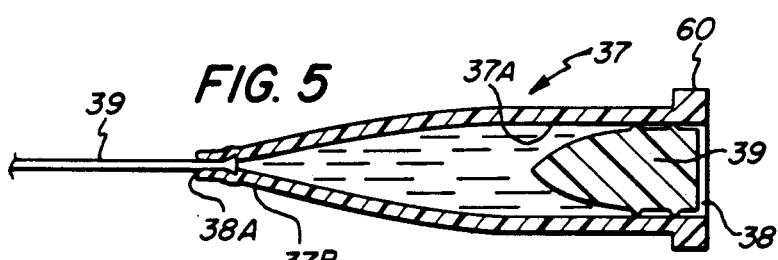
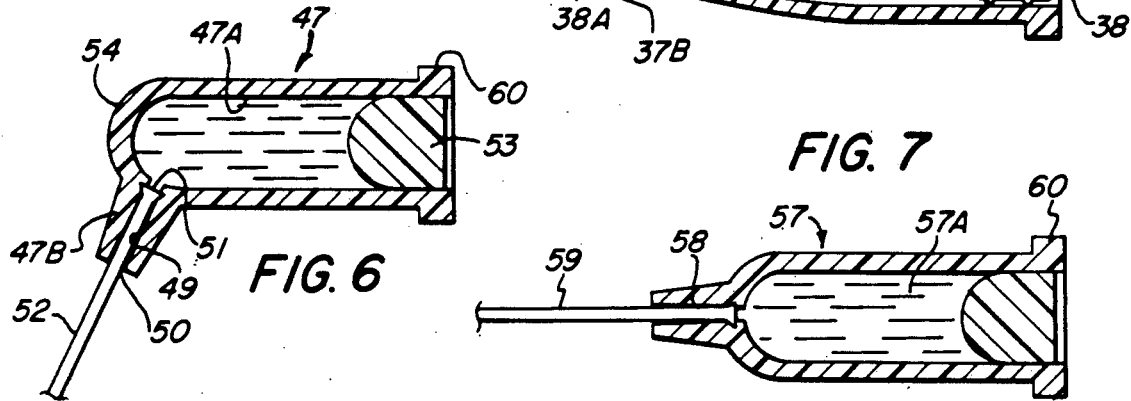

SYRINGE AND DISPOSABLE CAPSULE WITH CANNULA FOR USE THEREWITH

FIELD OF INVENTION

This invention is particularly directed to a dental syringe and/or disposable capsule for use therewith with a needle cannula.

PROBLEM AND PRIOR ART

Dental syringes and disposable capsules for use therewith have been known for some years. U.S. Pat. No. 3,581,399 issued to William B. Dragan is a known dental syringe utilized a disposable plastic capsule having a displaceable piston for extruding a dental material therefrom. U.S. Pat. Nos. 3,900,954 and 4,198,756 also issued to William B. Dragan, disclose other variations of disposable capsules and/or syringe holders for use therewith. Other patents directed to essentially the same concept or item have been granted as evidenced by U.S. Pat. Nos. 4,295,828; 4,330,280; 4,384,853 and 4,391,590. Each of these patents discloses essentially a similar type of disposable plastic capsule for use with a dental syringe or ejector. Essentially, the disposable tips comprise an all plastic body having a reservoir portion for containing a supply of material and having a piston or plug for sealing the material within the reservoir portion, and an angularly disposed discharge tip end through which the material is dispensed. The discharge tips being integrally formed of the material of the capsule, were generally relatively short and thus limited the dental procedures in which such capsules could be used. U.S. Pat. No. 4,682,950; U.S. Pat. No. Des. 289,682; U.S. Pat. No. Des. 292,825 and U.S. Pat. No. 4,768,954, also issued to William B. Dragan, disclose various other patented variations of a plastic capsule of the type disclosed initially in U.S. Pat. No. 3,581,399.

Plastic capsules having a needle cannula fixedly connected to the end of the capsule are also known. However, such cannular plastic capsules required the needle cannula to be molded in place onto the plastic capsule body or were adhesively secured to the tip end of the plastic caps. Each of these prior known needle capsules required specialized equipment and relatively complex manufacturing procedures to produce such cannular capsules. One such known cannula type capsule has been on sale by a company identified as Hygenic.

OBJECTS

An object of this invention is to provide an improved syringe and capsule for use therewith capable of performing certain dental procedures in a more facile manner than was heretofore possible.

Another object is to provide a disposable plastic capsule having an extended needle cannula defining the discharge orifice.

Another object is to provide a disposable plastic capsule having an extended needle cannula connected to the capsule so as to be rendered rotatably mounted relative thereto.

Another object is to provide a plastic capsule with a needle cannula that is both rotatably mounted and sealed at the point of connection.

Another object is to provide a plastic capsule having the needle cannula secured thereto in a relatively simple and expedient manner in which a positive seal is formed at the connection thereof while permitting the needle cannula to be rotatable independently of the capsule.

Another object resides in attaching the cannula to the plastic capsule in a positive manner without utilizing any adhesives or complex mechanical connection.

SUMMARY OF THE INVENTION

The foregoing objects and other features and advantages are attained by a syringe or ejector that includes a barrel having a plunger reciprocally mounted therein for movement between a retracted and protracted position. The forward end of the barrel is provided with an inturned flange to define a front opening. A longitudinally extending cut-out portion is disposed adjacent the front opening to define a seat for receiving the capsule. The longitudinal cut-out is formed in the upper circumferential portion of the barrel that extends to the front end. A capsule, adapted to be fitted to the seat defined so as to extend forwardly of the front end of the barrel, comprises a plastic body having a reservoir portion for containing a supply of material to be dispensed. Disposed within the open end of the body portion is a displaceable plug or piston for sealing the material within the reservoir and for ejecting the material therefrom when the piston is displaced by the actuation of the syringe plunger. Connected to the other end of the capsule is a discharge tip. In accordance with this invention, a needle cannula is fitted to the discharge tip to provide an extension thereof. The needle cannula is outwardly flared at one end thereof. The needle cannula is attached to the discharge tip by passing the unflared end of the cannula through the discharge tip from the reservoir side. By applying a force or pressure on the cannula, the flared end will bite into or become embedded in the material of the capsule defining the inner wall surface of the discharge tip as the flared end is provided with a diameter which is slightly greater than the inner diameter of the orifice opening of the discharge tip. The biting or embedding of the flared end of the nozzle effects both the sealing and rotatable journaling of the needles cannula to the tip end of the capsule.

FEATURES

A feature of this invention resides in the provision of providing a slotted opening in the upper circumferential portion of a syringe barrel to form a seal for receiving a disposable capsule therein.

Another feature resides in the provision of a plastic capsule having a needle cannula as an extension of the discharge tip whereby the needle cannula is rendered rotatable relative to the plastic capsule.

Another feature resides in rotatably journalling a metal needle cannula to a plastic capsule by a simple force fit.

Another feature resides in providing a needle cannula with a flared end portion for positively securing the cannula to the discharge end of a plastic capsule in a positive sealing relationship.

Other features and advantages will become more readily apparent when considered in view of the specification and drawings in which:

FIG. 1 illustrates a syringe construction embodying the present invention.

FIG. 2 illustrates a side view of a plastic capsule of the present invention for use with a syringe construction of a type shown in FIG. 1.

FIG. 3 is a detail view of a needle cannula embodying the invention.

FIG. 4 is an enlarged side sectional view of a capsule embodying the invention.

FIG. 5 is a sectional side view of a modified embodiment of a capsule of the present invention.

FIG. 6 is a sectional view of another modified embodiment.

FIG. 7 is a sectional view of still another modified embodiment.

DETAIL DESCRIPTION

Referring to the drawings, there is shown a dental syringe or ejector holder 10 adapted for use with a capsule construction as will be hereinafter defined. The illustrated syringe or ejector holder 10 comprises an elongated barrel 11 having a bore 12 extending therethrough. The forward end 11A of the barrel is provided with an inturned flange or shoulder 13 to define a front opening 14. In the illustrated embodiment, the upper circumferential portion is provided with a cut-out portion to define an elongated slot 15 which extends to the front opening 14. The cut out portion or slot 15 thus defines a circumferential bottom seat 16 for receiving the capsule 17, as will be hereinafter described. The arrangement of the seat 16 is such that it will support a capsule therein as shown. It will be understood that the barrel 11 may be formed of either metal or plastic. If made of metal, the capsule 17 can be readily press-fitted into the seat 16 formed in the end of the barrel. If the barrel is made of a resilient plastic material, the capsule can be snap-fitted and retained within the seat. This is readily attained by providing the seat forming portion 16 of the barrel with a circumference having slightly more than 180°. Thus, the inherent resiliency between the capsule 17 and the end walls of the barrel 11 defining the seat 16 will positively secure and retain the capsule in position within the seat 16. By forming the seat 16 so that it forms a bottom support for the capsule, the danger of the capsule becoming separated from its seat 16 in case of wear or excessive tolerance between the dimensions of the capsule and seat is greatly minimized.

Reciprocally mounted within the bore 12 of the syringe barrel 11 is a plunger 18 which is movable between a retracted and protracted position relative to the barrel. As shown in FIG. 1, the other end of the barrel 11B is connected to a suitable handle 19 to which a pivoting actuating lever 20 is connected. The arrangement is such that the lever 20 is disposed in bearing relationship with the end 18A of the plunger to effect the reciprocal movement thereof when the actuating lever is squeezed toward the fixed handle 19 in a manner similar to that initially disclosed in U.S. Pat. No. 4,198,756 and subsequently utilized in U.S. Pat. Nos. 4,295,828; 4,330,280 and 4,384,853.

In accordance with this invention, the capsule 17 for use with the syringe construction described comprises a plastic body 17A which is preferably injection molded of a suitable plastic material, e.g. zetel nylon, polyethylene, polypropylene and the like to define a reservoir portion 17B and a connected integrally molded discharge tip 17C. As shown, the reservoir portion is formed with a cylindrical shape having a full open 21 at one end thereof through which the dental material M may be loaded into the reservoir portion 17B. The tip end connected to the other end of the reservoir portion 17B in the embodiment of FIGS. 2 and 4 is angularly disposed relative to the longitudinal axis of the reservoir portion. As shown, the inner walls of the capsule 17 in the vicinity of the discharge end 17C taper inwardly toward the orifice 22. A plug or displaceable piston 23 is fitted in the open end of the reservoir to seal the material M therein. The piston 23 may be provided with slight circumferential fins to enhance the sealing between the internal walls of the reservoir portion 17B and the external walls of the piston. Also, the leading end of the piston 23 may be provided with a shape complementing the forward end walls of the capsule 17 so as to ensure maximum evacuation of the material M from the capsule when the piston 23 is displaced.

In accordance with this invention, a needle cannula 24 is extended through the orifice defined in the tip end 17C. As best seen in FIG. 3, the needle cannula 24 comprises a metal needle having a gauge size that can range between 14 to 30 and a predetermined length to define an extension of the discharge tip end 17C. In accordance with this invention, the needle cannula is outwardly flared at one end as indicated as 24A. The outer diameter D of the flared end is sized so as to be slightly greater than the internal diameter of the orifice 22 formed on the tip end 17C. Generally, the orifice opening 22 may range between 0.5 to 2.0 mm or thereabouts. To positively connect the needle cannula to the end of the discharge tip portion 17C, the needle cannula is inserted into the open end of the capsule so that the flared end is trailing the front opening 25 of the needle cannula. The needle cannula is then pushed or pulled through the orifice 22 until the rim of the flared end is pinched or imbedded into the internal wall surface of the discharge tip end 17C. As best seen in FIG. 3, the force or pressure applied to the needle cannula 24 will cause the flared end 24A to bite into the material of the capsule adjacent the discharge tip orifice 22. The arrangement is such that the needle cannula 24 is thus set in place so that it cannot be projected or separated from the capsule during the ejection of the material M and the biting of the flared end within the material of the capable functions as a barb or one-way stop that will prohibit the cannula 24 from being forced rearwardly back into the capsule. The connection thus described provides a positive seal between the cannula 24 and the tip end 17C of the capsule to prohibit any material to extrude around the flared end of the cannula 24 during the ejection of the material M, and at the same time allowed the needle cannula 24 to be rotated relative to the capsule, allowing a dentist or user to direct the opening 25 of the cannula in any desired angular position. It will be understood that the needle cannula is sufficiently bendable so that a dentist can bend the needle to assume any desired angle, see FIGS. 1, 2 and 4 and as the needle cannula can be rotated relative to the capture body, the dentist is able to perform procedures which could not be readily achieved by the capsule per se. For example, the capsule with needle cannula as herein described is particularly suitable for placing dental material in a deep area, e.g. in root canal procedures, or in setting a post in a tooth, or in any procedure wherein a specific dental material is required to be precisely placed in a difficult, small or hard to reach cavity or space within a patient's mouth.

As described, the cannula is economically and expediently secured in place within the discharge end of a plastic capsule without the need of any special adhesive or securing tools or equipment. An application of a simple force on the needle cannula 24 is sufficient to seal and rotatably journal the needle cannula 24 to the discharge end of a plastic capsule 17. It will be understood that the capsule 17 per se may be formed of a plastic material so as to be rendered light opaque for the handling and placement of various light curable materials currently being widely used, or can be made of a clear or transparent material or of any color in between. It will also be understood that the capsule with cannula can be preloaded with a predetermined amount of material M, e.g. at a factory, and sold in a preloaded state, or the capsule with cannula could be distributed in an empty state whereby it can be loaded by the dentist or an assistant with the dentist's preferred brand of material.

FIG. 5 illustrates a modified capsules 37. In this form, the capsule is provided with a cylindrical reservoir portion 37A which is open at one end 38, and which is provided with an axially disposed discharge end portion 37B. Extended through the axially disposed orifice 38A at the discharge end is a needle cannula 39 which is similar in construction and attachment to the capsule as hereinbefore described. A plug or piston 39 seals the open end of the reservoir. In all other respects, the capsule and cannula of FIG. 5 is similar to that hereinbefore described.

FIG. 6 illustrates a slightly modified embodiment of a capsule and cannula construction embodying the invention. In this form, the capsule 47 is provided with a cylindrical reservoir portion 47A terminating in a discharge tip 47B having bore 49 extending therethrough to define the orifice opening 50. The inner end wall of the capsule may be provided with a hemispherical end wall 54 as shown. In this embodiment, the bore 49 is formed during the molding of the capsule 37 by a core pin. Thus, inherent in the forming of the capsule 37 by molding, the inner wall surface of the bore 49 will normally be tapered inwardly toward the reservoir portion to a slight degree. The inherent inward taper of bore 49 is made sufficient for the flared end 51 of cannula 52 to bite or imbed itself into the material of the discharge tip 47B as hereinbefore described. The open end of the reservoir 47A is sealed by a piston 53 having a complementary shape to complement the end wall of the capsule 47. In all other respects, the construction, mode of operation and function are similar to that hereinbefore described.

FIG. 7 illustrates another modified capsule 57 which is similar in construction to that of FIG. 8 with the exception that the discharge tip 58 is axially disposed rather than angularly disposed relative to the longitudinal axis of the reservoir portion 57A. In all other respects, the construction and attachment of the needle cannula 59 is similar to that herein described.

Each of the described capsules includes a laterally extending flange 60, circumscribing the open end of the respective capsules. In use, the capsule flange 60 is disposed adjacent the inturned end wall of the syringe or ejector so as to restrain the capsule from being forced through the front opening of the syringe barrel during ejection or extruding of the material from the capsule. (See FIG. 1).

It will be understood that in the event the capsules herein described are preloaded at a factory with a particular type of dental material, that the end of the needle can be sealed in any suitable manner as, for example, by an end cap or by taping over the orifice of the needle with suitable adhesive type tape or materials. In this manner, the contents of the capsules are protected from foreign matter and/or light in the event that the material contained within the capsule comprises any of the light activated dental materials.

From the foregoing, it will be apparent that the described cannula capsules comprise a relatively simply structure in which the cannula is both rotatably journalled and sealed in a simple and expedient manner by a force fit that prohibits any linear displacement between the needle cannula and associated capsule during normal use. Further, the described capsules can be interchangeably used with any of the existing syringes as well as with the improved syringe construction herein described. The needle cannula capsule as described also permits precise placement of various dental materials in procedures not feasible by the prior injection molded capsules.

While the invention has been described with respect to various embodiments thereof, it will be appreciated and understood that various modifications and embodiments thereof can be made without departing from the spirit or scope of the invention.

What is claimed is:

1. A capsule having a plastic body portion defining a reservoir for containing a predetermined amount of material and a connected discharge tip having an orifice, a needle cannula having a bore extending therethrough, said needle cannula being projected through said orifice of said discharge tip to extend beyond the end of said discharge tip, and said needle cannula having means formed at an end thereof with said means being of one piece with said cannula for positively retaining, sealing and rotatably connecting said cannula relative to said discharge tip for 360 degree rotation relative to said discharge tip.

2. A capsule as defined in claim 1, wherein said body portion has an open end opposite said discharge tip, and a displaceable piston sealing the open end of said body portion for sealing the material within said reservoir and for ejecting the material through said cannula when said piston is displaced within said body portion.

3. A capsule having a plastic body portion defining a reservoir having an opened end for containing a predetermined amount of material to be dispensed and a connected discharge tip having a discharge orifice, a needle cannula having a bore extending therethrough, said needle cannula being projected through said discharge orifice to extend beyond the end of said discharge tip, and means for sealing and rotatably connecting said cannula relative to said discharge tip, said means comprising a flared end formed at one end of said cannula, said flared end being forceably imbedded in the internal wall of said discharge tip adjacent said discharge orifice for sealing and rotatably connecting said needle cannula for 360° rotation relative to said discharge tip.

4. A capsule as defined in claim 3, wherein said discharge tip and connected cannula are angularly disposed relative to the longitudinal axis of said reservoir.

5. A capsule as defined in claim 3, wherein said discharge tip and connected cannula are axially disposed relative to said reservoir.

6. A capsule as defined in claim 3, wherein the flared end of said cannula has an outer diameter which is slightly greater than the minimum internal diameter of said discharge tip.

7. A capsule as defined in claim 3 wherein said discharge tip has a tapering internal wall surface, and said needle cannula having an outwardly flared end portion, said outwardly flared portion being imbedded in said tapering internal wall surface of said discharge tip to rotatably secure said cannula to said discharge tip in sealing relationship therewith.

8. A capsule as defined in claim 7 wherein said discharge tip has a discharge end, and said discharge tip tapers inwardly toward said discharge end.

9. A capsule as defined in claim 7, wherein said discharge tip tapers slightly inwardly toward the said reservoir.

10. A capsule as defined in claim 3 wherein the material of said capsule is light opaque.

11. A capsule as defined in claim 3, wherein the material of said capsule is light transparent.

12. A capsule as defined in claim 3, wherein the capsule may be variously colored by suitably pigmenting the material of which it is formed.

13. A capsule as defined in claim 3 and including an outwardly extending flange about the open end of said reservoir.

14. A capsule as defined in claim 3 and including a predetermined amount of material within the reservoir portion of the capsule, a displaceable piston for sealing said material within said reservoir and means for sealing the extended end of said cannula.

15. A capsule for containing and dispensing a material in a precise manner comprising a body portion defining a reservoir for containing a predetermined amount of material, said body portion being open at one end for receiving the material, and said body portion having a discharge tip formed at the other end of said body portion, said discharge tip end being integrally formed with said body portion and having an orifice opening therein, and a cannula having a bore extending through said orifice opening, said cannula being outwardly flared at one end thereof, said outwardly flared end having a diameter slightly greater than said orifice opening, and said cannula extending through said discharge tip to protect through said orifice opening, said flared end being forceably imbedded in the internal surface of said discharge tip to define a seat thereat adjacent said orifice opening, and whereby said cannula is rendered rotatably mounted for 360° rotation relative to said capsule within said discharge tip in sealing relationship therewith.

16. In combination, a syringe holder comprising a barrel having a bore extending therethrough, a plunger slidably mounted between a protracted and retracted position within said bore, a capsule contacting a predetermined amount of material, means for detachably connecting said capsule to the end of said barrel, said capsule having a body portion defining a reservoir for containing a predetermined amount of material to be dispensed, a displaceable piston for sealing said material within said reservoir, a discharge tip connected in communication with said reservoir, said discharge tip terminating in a discharge orifice, a needle cannula projecting through said discharge orifice to define an extension thereof, said needle cannula having a flared portion at one end thereof, and said flared end being imbedded in the internal wall surface of said discharge tip adjacent said orifice whereby said cannula is rotatably connected to said tip in sealing relationship for 360° rotation relative thereto.

17. The combination as defined in claim 16, wherein said means for detachably connecting said capsule to said barrel comprises a longitudinally extending cut out portion formed adjacent the front end of the barrel to define a seat for receiving said capsule, said barrel having an opened front end, and an inturned shoulder defining said front end, and said capsule having a laterally extending flange circumscribing said reservoir whereby said flange is disposed in engaging position with said shoulder.

18. The combination as defined in claim 17, wherein said cut out portion is disposed in the top portion of said barrel.

* * * * *